United States Patent [19]

Mobilio

[11] Patent Number: 5,055,590
[45] Date of Patent: Oct. 8, 1991

[54] PREPARATION OF 2,3,4,9-TETRAHYDRO-1H-CARBAZOLE ACETIC ACID DERIVATIVES

[75] Inventor: Dominick Mobilio, Franklin Park, N.J.

[73] Assignee: American Home Products Corporation, New York, N.Y.

[21] Appl. No.: 491,369

[22] Filed: Mar. 9, 1990

Related U.S. Application Data

[62] Division of Ser. No. 415,159, Sep. 29, 1989, Pat. No. 4,927,842.

[51] Int. Cl.$^5$ .......................................... C07D 209/82
[52] U.S. Cl. .................................................. 548/439
[58] Field of Search ................................ 548/439, 440

[56] References Cited

U.S. PATENT DOCUMENTS

| | | |
|---|---|---|
| 3,939,178 | 2/1976 | Demerson et al. ................. 548/439 |
| 4,578,398 | 3/1986 | Mobilio et al. ...................... 548/439 |
| 4,584,312 | 4/1986 | Mobilio et al. ...................... 548/439 |
| 4,616,028 | 10/1986 | Mobilio et al. ...................... 548/439 |
| 4,782,076 | 11/1988 | Mobilio et al. ...................... 548/439 |
| 4,783,479 | 11/1988 | Mobilio ............................... 548/439 |

Primary Examiner—Mary C. Lee
Assistant Examiner—Robert C. Whittenbaugh
Attorney, Agent, or Firm—Walter Patton

[57] ABSTRACT

Substituted 2,3,4,9-tetrahydro-1H-carbazole-1-acetic acid derivatives and methods for their preparation and use are disclosed. The compounds are useful anti-inflammatory agents.

2 Claims, No Drawings

PREPARATION OF 2,3,4,9-TETRAHYDRO-1H-CARBAZOLE ACETIC ACID DERIVATIVES

This is a divisional application of copending application U.S. Ser. No. 07/415,159 filed Sept. 29, 1989, now issued as U.S. Pat. No. 4,927,842.

BACKGROUND OF THE INVENTION

1. Field of Invention

This invention relates to tricyclic acetic acid derivatives, to their preparation and use, and to intermediates used for their preparation.

More specifically, this invention relates to tricyclic acetic acid derivatives in which the tricyclic portion thereof is characterized by having an indole portion fused to a cyclohexane ring. Still more specifically, the compounds of this invention are characterized as derivatives of the following tricyclic acetic acid system:

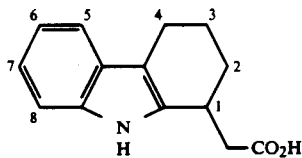

2,3,4,9-tetrahydro-1H-carbazole-1-acetic acid in which the carbons at the 1-, 4-, 5-, 6-, 7- and 8-positions are further substituted.

The tricyclic acetic acid compounds of this invention possess useful pharmacologic properties; for instance, they exhibit anti-inflammatory activity at dose levels which do not elicit undesirable side effects. The foregoing combination of attributes renders the compounds of this invention useful for the treatment of inflammatory conditions in a mammal.

2. Prior Art

The closest prior art to the present invention is:

U.S. Pat. Nos. 4,847,389; 4,783,479; 4,782,076; 4,709,048; 4,701,533; 4,687,860; 4,616,028; 4,584,312 and 4,578,398.

Demerson et al, U.S. Pat. No. 3,939,178 discloses 1,3,4,9-tetrahydropyrano[3,4-b]indoles and 1,3,4,9-tetrahydrothiopyrano[3,4-b]indoles having analgesic and anti-inflammatory activity.

Boehringer Mannheim European Patent 42593 generically discloses starting materials useful for producing cardiotonic and beta-blocking agents. The starting materials include 1,2,3,4-tetrahydrocarbazoles with substituents selected from the broad group including hydrogen, carboxy, lower alkyl and lower alkenyl. The starting materials are in each case also substituted with a reactive group which distinguishes them from the compounds of the present invention.

SUMMARY OF THE INVENTION

The compounds of this invention are represented by formulas (I) and (II)

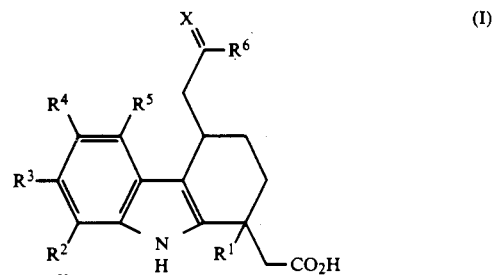

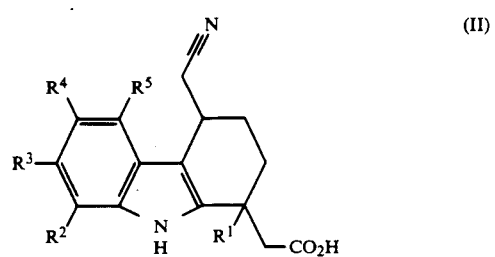

wherein $R^1$ is lower alkyl containing one to six carbon atoms; $R^2$ to $R^5$ are independently selected from the group consisting of H, lower alkyl containing one to six carbon atoms, halogen and haloalkyl containing one to six carbon atoms; $R^6$ is H, lower alkyl containing one to six carbon atoms; X is O, NOH, or NO-alkyl wherein alkyl contains one to six carbon atoms; and the pharmaceutically acceptable salts thereof.

A preferred aspect of this invention is represented by compounds of formulas (III) and (IV)

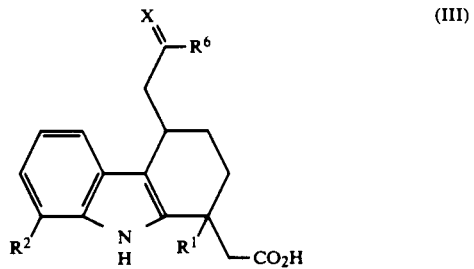

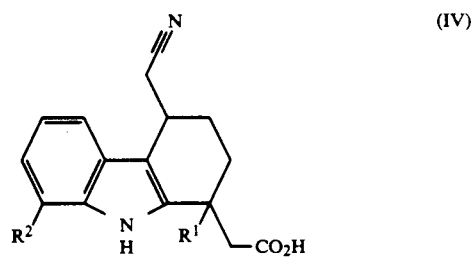

wherein $R^1$ is methyl or ethyl; $R^2$ is H, methyl or ethyl; $R^6$ is H, methyl or ethyl; X is O, NOH or NOMe; and the pharmaceutically acceptable salts thereof.

A still further preferred aspect of the present invention are the compounds represented by compounds of formulas (V) and (VI)

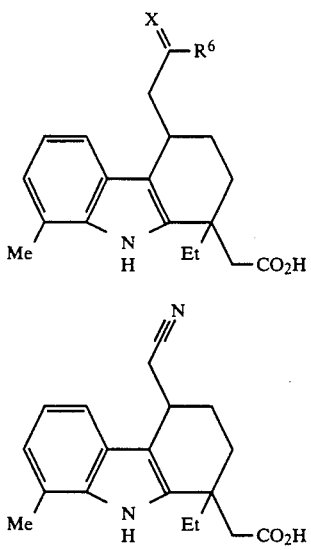

(V)

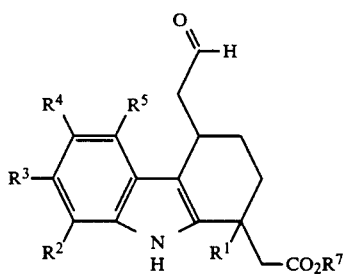

(VI)

wherein $R^6$ is H or methyl and X is O, NOH or NOMe; and the pharmaceutically acceptable salts thereof.

The most preferred compounds of the present invention are designated cis-1-ethyl-2,3,4,9-tetrahydro-4-[2-(hydroxyimino)ethyl]-8-methyl-1H-carbazole-1-acetic acid;

cis-1-ethyl-2,3,4,9-tetrahydro-4-[2-(methoxyimino)ethyl]-8-methyl-1H-carbazole-1-acetic acid cis-1-ethyl-2,3,4,9-tetrahydro-8-methyl-4-(2-oxopropyl)-1H-carbazole-1-acetic acid;

cis-4-(cyanomethyl)-1-ethyl-2,3,4,9-tetrahydro-8-methyl-1H-carbazole-1-acetic acid;

and the pharmaceutically acceptable salts thereof.

The compounds of the present invention represented by formula (I) wherein $R^1$ is lower alkyl containing one to six carbon atoms; $R^2$ to $R^5$ are independently selected from the group consisting of H, lower alkyl containing one to six carbon atoms, halogen and haloalkyl containing one to six carbon atoms; $R^6$ is H, and X is NOH or NO-alkyl wherein alkyl contains one to six carbon atoms are prepared by a process in which the aldehyde of formula (VII)

(VII)

wherein $R^1$ is lower alkyl containing one to six carbon atoms; $R^2$ to $R^5$ are independently selected from the group consisting of H, lower alkyl containing one to six carbon atoms, halogen and haloalkyl containing one to six carbon atoms; $R^7$ is lower alkyl containing one to six carbon atoms, prepared as described in U.S. Pat. No. 4,701,533 is treated with hydroxylamine hydrochloride or alkyl-ONH$_2$-HCl to form the ester of a compound of formula (I) wherein $R^1$ is lower alkyl containing one to six carbon atoms; $R^2$ to $R^5$ are independently selected from the group consisting of H, lower alkyl containing one to six carbon atoms, halogen and haloalkyl containing one to six carbon atoms; $R^6$ is H, and X is NOH or NO-alkyl wherein alkyl contains one to six carbon atoms. After hydrolysis of the ester, a compound of formula (I) wherein $R^1$ to $R^6$ and X are as defined above is obtained.

The transformation may be carried out by mixing the aldehyde of formula (VII) with hydroxylamine hydrochloride or an alkyl-ONH$_2$-HCl in an inert solvent in the presence of a base. Preferably, the aldehyde (VII) can be dissolved in ethanol and treated with an aqueous solution of hydroxylamine hydrochloride containing sodium acetate or the aldehyde (VII) can be dissolved in ethanol containing pyridine and treated with the alkyl-ONH$_2$-HCl.

The esters of formula (I) thus obtained wherein $R^1$ is lower alkyl containing one to six carbon atoms; $R^2$ to $R^5$ are independently selected from the group consisting of H, lower alkyl containing one to six carbon atoms, halogen and haloalkyl containing one to six carbon atoms; $R^6$ is H, and X is NOH can be treated with acid to form the ester of the nitrile compound of formula (II) wherein $R^1$ is lower alkyl containing one to six carbon atoms; $R^2$ to $R^5$ are independently H, lower alkyl containing one to six carbon atoms, halogen and haloalkyl containing one to six carbon atoms. After hydrolysis of the ester, the nitrile compound of formula (II) is obtained wherein $R^1$ to $R^5$ are as defined above.

The transformation of the oxime to the nitrile may be carried out in an inert solvent in the presence of an acid at temperatures ranging from room temperature to the boiling point of the solvent. Preferably, the reaction is carried out in refluxing ethanol in the presence of a small amount of concentrated hydrochloric acid.

The nitrile compounds of formula (II) thus obtained can be treated with a trialkylaluminum reagent to form a compound of formula (I) wherein $R^1$ is lower alkyl containing one to six carbon atoms; $R^2$ to $R^5$ are independently H, lower alkyl containing one to six carbon atoms, halogen and haloalkyl containing one to six carbon atoms; $R^6$ is lower alkyl containing one to six carbon atoms and X is O. The reaction may be carried out in the presence of a catalyst such as Ni(acac)$_2$ preferably by stirring the ester of formula (II) in toluene containing Ni(acac)$_2$ and treating the reaction mixture with a trialkylaluminum reagent such as trimethylaluminum.

Also, the compounds of formula (I) thus obtained can be treated with hydroxylamine hydrochloride or alkyl-ONH$_2$-HCl as described above to form a compound of formula (I) wherein $R^1$ is lower alkyl containing one to six carbon atoms; $R^2$ to $R^5$ are independently H, lower alkyl containing one to six carbon atoms, halogen and haloalkyl containing one to six carbon atoms; $R^6$ is lower alkyl containing one to six carbon atoms and X is NOH, NOMe or NO-alkyl containing one to six carbon atoms.

The subsequent conversion of the lower alkyl ester tricyclic compounds of formulas (I) or (II) to the corresponding compounds of formulas (I) or (II) is effected readily by subjecting the tricyclic compound to hydrolysis. Generally speaking, this conversion is most conveniently performed by employing a base as the hydrolyzing agent. The hydrolysis is performed in the presence of sufficient water optionally under an inert atmosphere, followed by acidification of the reaction mixture to yield the desired compound of formula (I) or (II). However, the manner of hydrolysis is not intended to be limited to basic hydrolysis since hydrolysis under acidic conditions and other variations, for example, treatment with lithium iodide in collidine (see L. F. Fieser and M. Fieser, "Reagents for Organic Synthesis", John Wiley and Sons, Inc., New York, 1967, pp. 615–617) are also applicable.

For basic hydrolysis, a preferred embodiment involves subjecting the tricyclic ester to the action of a base, for example, sodium or potassium carbonate, in the presence of sufficient water to effect hydrolysis of the ester. The hydrolysis is performed using a suitable solvent, for example, methanol or ethanol under a nitrogen atmosphere.

The reaction mixture is maintained at a temperature of from 25° C. to the reflux temperature until hydrolysis occurs. Usually from 10 minutes to 48 hours is sufficient for this hydrolysis. The reaction mixture is then rendered acidic with an acid, for example, acetic acid, hydrochloric acid, sulfuric acid and the like, to release the free acid as a solid.

Alternatively, the tricyclic ester is hydrolyzed by subjecting the ester to the action of a hydrolyzing agent which is a strong organic or inorganic acid, for example, trifluoroacetic acid, p-toluenesulfonic acid, hydrochloric acid, hydrobromic acid, hydroiodic acid, sulfuric acid, phosphoric acid and the like in a suitable solvent at a temperature of at least 60° C. and preferably from 90° C. to the boiling point of the mixture until the hydrolysis occurs. Usually from 5 to 48 hours are required for this hydrolysis. Suitable solvents include water, acetic acid, aqueous alcohols and the like. If acid hydrolysis is used, the free acid is formed directly. If necessary, the reaction mixture can be diluted with water to precipitate the product. In the case of a compound of formula (I) wherein X is NOH, elimination of water to produce the nitrile in the presence of strong acid might preclude the use of acidic conditions for ester hydrolysis.

DETAILED DESCRIPTION OF THE INVENTION

The term "lower alkyl" as used herein contemplates straight chain alkyl radicals containing from one to six carbon atoms and branched chain alkyl radicals containing from three to four carbon atoms and includes methyl, ethyl, propyl, isopropyl, butyl, isobutyl, pentyl, hexyl and the like.

The term "halogen" as used herein includes fluorine, chlorine, bromine and iodine.

The compounds of formulas (I) and (II) form salts with suitable pharmaceutically acceptable inorganic and organic bases. These derived salts possess the same activity as the parent acid and are included within the scope of this invention. The acid of formula (I) or (II) is transformed in excellent yield into the corresponding pharmaceutically acceptable salts by neutralization of said acid with the appropriate inorganic or organic base. The salts are administered in the same manner as the parent acid compounds. Suitable inorganic bases to form these salts include, for example, the hydroxides, carbonates, bicarbonates, or alkoxides of the alkali metals or alkaline earth metals, for example, sodium, potassium, magnesium, calcium and the like. Suitable organic bases include the following amines; lower mono-, di- and tri-alkylamines, the alkyl radicals of which contain up to three carbon atoms, such as methylamine, dimethylamine, trimethylamine, ethylamine, di- and triethylamine, methylethylamine, and the like; mono, di- and trialkanolamines, the alkanol radicals of which contain up to three carbon atoms, such as mono-, di- and triethanolamine; alkylenediamines which contain up to six carbon atoms, such as hexamethylenediamine; amino sugars, such as glucosamine; phenyl substituted alkylamines, such as benzenemethanamine or N,N-bis-(phenylmethyl)-1,2-ethanediamine; cyclic saturated or unsaturated bases containing up to six carbon atoms, such as pyrrolidine, piperidine, morpholine, piperazine and their N-alkyl and N-hydroxyalkyl derivatives, such as N-methylmorpholine and N-(2-hydroxyethyl)piperidine, as well as pyridine. Furthermore, there may be mentioned the corresponding quaternary salts, such as the tetraalkyl (for example tetramethyl), alkyl-alkanol (for example methyltrimethanol and trimethyl-monoethanol) and cyclic ammonium salts, for example, the N-methyl-pyridinium, N-methyl-N-(2-hydroxyethyl)-morpholinium, N,N-dimethyl-morpholinium, N-methyl-N-(2-hydroxyethyl)-morpholinium, N,N-dimethyl-piperidinium salts, which are characterized by good water solubility. In principle, however, there can be used all the ammonium salts which are physiologically compatible.

The transformations to the salts can be carried out be a variety of methods known in the art. For example, in the case of the inorganic salts, it is preferred to dissolve the acid of formula (I) or (II) in water containing at least one equivalent amount of a hydroxide, carbonate, or bicarbonate corresponding to the inorganic salt desired. Advantageously, the reaction is preformed in a water-miscible organic solvent inert to the reaction conditions, for example, methanol, ethanol, dioxane, and the like in the presence of water. For example, such use of sodium hydroxide, sodium carbonate or sodium bicarbonate gives a solution of the sodium salt. Evaporation of the solution or addition of a water-miscible solvent of a more moderate polarity, for example, a lower alkanol, for instance, butanol, or a lower alkanone, for instance, ethyl methyl ketone, gives the solid inorganic salt if that form is desired.

To produce an amine salt, the acid of formula (I) or (II) is dissolved in a suitable solvent of either moderate or low polarity, for example, ethanol, acetone, ethyl acetate, diethyl ether and benzene. At least an equivalent amount of the amine corresponding to the desired cation is then added to that solution. If the resulting salt does not precipitate, it can usually be obtained in solid form by addition of a miscible diluent of low polarity, for example, benzene or petroleum ether, or by evaporation. If the amine is relatively volatile, any excess can easily be removed by evaporation. It is preferred to use substantially equivalent amounts of the less volatile amines.

Salts wherein the cation is quaternary ammonium are produced by mixing the acid of formula (I) or (II) with an equivalent amount of the corresponding quaternary ammonium hydroxide in water solution, followed by evaporation of the water.

Included in the present invention are the diastereoisomers wherein the 4-substituent is either cis or trans to the acetic acid chain at position one.

Also included in this invention are the optical isomers of the compounds of formula (I) and (II) which result from asymmetric centers, contained therein. Such isomers are obtained in substantially pure form by classical separation techniques and by sterically controlled synthesis.

Anti-inflammatory Activity

The useful anti-inflammatory activities of the tricyclic acetic acid derivatives of formula (I) are demonstrated in standard pharmacologic tests, for example, the test designated: PREVENTATIVE ADJUVANT EDEMA.

The objective of this test is to determine the ability of test drugs to exhibit an acute anti-inflammatory effect in rats. This test is a primary screen for anti-inflammatory drugs.

Species

Male Sprague Dawley rats (180-200 g) are used. The animals have free access to water but food is withdrawn 18 hours before testing.

Drug Preparations and Administration

Freund's complete adjuvant is prepared by suspending 5 mg killed and dried Mycobacterium butyricum (Difco) in 1 mL mineral oil. The test compounds are dissolved in distilled water or suspended in 0.5% Tween 80 in distilled water according to their solubility. For primary screening all drugs are administered by gastric lavage at the arbitrary dosage of 25 mg/kg, p.o. in a volume of 0.5 mL/100 g body weight to groups of 10 animals.

Methodological Details

The method is essentially that described by Wax et al, J. Pharmacol. Exp. Ther., 192, 166-171 (1975). Groups of rats are injected intradermally in the left hind paw with 0.1 mL of Freund's complete adjuvant. The test compound or vehicle is administered immediately before the adjuvant, 24 hours and 48 hours after the adjuvant (day 0, 1 and 2). The injected hind paw volume is measured before the injection of adjuvant and 24 hours after the last drug administration (day 3) by means of a plethysmometer (Buxco Electronics Inc.). The difference between the hind paw volume on day 0 and day 3 represents the edema volume. Etodolac (25 mg/kg, p.o.) is included as a positive control.

Presentation of Results

The mean edema volume (expressed as mL±SEM) is calculated for each group and the percentage protection conferred by the drug is calculated:

$$\% \text{ protection} = \frac{(c - t)100}{c}$$

where c is the mean edema volume for the untreated controls and t is the mean edema volume for the drug treated group.

| | Preventative Adjuvant Edema | |
|---|---|---|
| Example | Dose (mg/kg, p.o.) | % Inhibition |
| 1 | 25 | 59 |
| 2 | 25 | 45 |
| 3 | 25 | 52 |
| 4 | 25 | 52 |

The lack of side effects for the compounds of this invention are demonstrated by standard acute toxicity tests described by R. A. Turner in "Screening Methods in Pharmacology", Academic Press, New York and London, 1965, pp. 152-163 and by prolonged administration of the compound to warm-blooded animals.

When the compounds of this invention are employed as anti-inflammatory agents in warm-blooded animals, they are administered orally, alone or in dosage forms, i.e., capsules or tablets, combined with pharmacologically acceptable excipients, such as starch, milk sugar and so forth, or they are administered orally in the form of solutions in suitable vehicles such as vegetable oils or water. The compounds of this invention may be administered orally in sustained release dosage form or transdermally in ointments or patches. The compounds of this invention may also be administered in the form of suppositories.

The dosage of the compounds of formula (I) and (II) of this invention will vary with the particular compound chosen and form of administration. Furthermore, it will vary with the particular host under treatment. Generally, the compounds of this invention are administered at a concentration level that affords protective effects without any deleterious side effects. These anti-inflammatorily effective concentration levels are usually obtained within a therapeutic range of 1.0 µg to 500 mg/kg per day, with a preferred range of 10 µg to 100 mg/kg per day.

The compounds of this invention also possess antipyretic activity.

The compounds of this invention may be administered together with the usual doses of caffeine.

The following examples further illustrate this invention.

EXAMPLE 1 cis-1-Ethyl-2,3,4,9-tetrahydro-4-[2-(hydroxyimino)ethyl]-8-methyl-1H-carbazole-1-acetic Acid A solution of cis-1-ethyl-2,3,4,9-tetrahydro-8-methyl-4-(2-oxoethyl)-1H-carbazole-1-acetic acid methyl ester (3.36 mmol, 1.10 g) in 36.6 mL of ethanol was treated dropwise under nitrogen with a solution of sodium acetate (5.04 mmol, 413 mg) and hydroxylamine hydrochloride (4.70 mmol, 327 mg) in 11.2 mL of water. After 15 minutes, the ethanol was removed with a rotary evaporator and replaced with 50 mL of ether. The mixture was washed with 2×40 mL of water and the extracts were back-extracted with 3×30 mL of ether. The organic phases were combined, dried over magnesium sulfate and concentrated in vacuo affording 1.15 g (3.36 mmol, 100%) of cis-1-ethyl-2,3,4,9-tetrahydro-4-[2-(hydroxyimino)ethyl]-8-methyl-1H-carbazole-1-acetic acid methyl ester as a yellow solid. Of this, 1.1 g (3.2 mmol) were stirred under nitrogen in 25.7 mL of methanol containing 3.22 mL of water and 4.18 mmol (578 mg) of potassium carbonate. After heating at reflux for 5 hours, and stirring at room temperature for 16 hours, the methanol was removed on a rotary evaporator and the residue was treated with 100 mL of 1N hydrochloric acid. The mixture was extracted with ether (4×40 mL) dried over magnesium sulfate and concentrated in vacuo giving a golden brown foam. Analysis by thin layer chromatography (35% ethyl acetate in petroleum ether) indicated a higher $R_f$ impurity overlapping with the desired oxime. Flash chromatography (50 mm diameter column, 5.5" of 2% phosphoric acid in methanol treated silica gel, 25% to 35% ethyl acetate in petroleum ether eluent) afforded 915 mg (2.79 mmol, 87%) of product which was recrystallized from 10% ethyl acetate in petroleum ether. Collected were 685 mg of the title compound as a pale yellow powder which was dried in vacuo at 85° C. (silica desiccant) for 8 hours: mp 173.5°–175.5° C.

$^1$H NMR (DMSO-d$_6$, 400 MHz, mixture of E/Z oxime isomers): δ0.7 (m), 1.6–2.1 (m), 2.4–2.6 (m), 2.6–2.74 (m), 3.06 (m), 3.32 (m), 6.72 (t), 6.8 (m), 7.24 (t), 7.32 (t), 10.3 (s), 10.36 (s), 10.73 (s), 11.1 (broad m).

IR (KBr, cm$^{-1}$): 3400, 3350, 3050, 2960, 2930, 2500, 1690.

Anal. Calcd. for C$_{10}$H$_{15}$NO$_7$: C, 69.49; H, 7.37; N, 8.53. Found: C, 69.76; H, 7.46; N, 8.41.

EXAMPLE 2 cis-1-Ethyl-2,3,4,9-tetrahydro-4-[2-(methoxyimino)ethyl]-8-methyl-1H-carbazole-1-acetic Acid A solution of cis-1-ethyl-2,3,4,9-tetrahydro-8-methyl-4-(2-oxoethyl)-1H-carbazole-1-acetic acid methyl ester (1.2 g, 3.7 mmol) in 14.3 mL of ethanol and 3.7 mL of pyridine was treated with 4.22 mmol (352 mg) of NH$_2$OMe.HCl. After 1.5 hours, another 465 mg (1.30 mmol) of NH$_2$OMe.HCl were added and the reaction mixture was stirred an additional 1.5 hours. The mixture was then concentrated in vacuo and redissolved in 60 mL of ether. The mixture was washed with 2×25 mL of 1N hydrochloric acid, and the extracts were back-extracted with ether (3×15 mL). The pooled organic phases were dried over magnesium sulfate and concentrated in vacuo affording 1.25 g (3.51 mmol, 96%) of a yellow foam. Of this, 3.37 mmol (1.20 g) were stirred under nitrogen in 27.6 mL of methanol containing 3.4 mL of water and 4.04 mmol (558 mg) of potassium carbonate, and heated at reflux for 6 hours, stirred at room temp for 16 hours, then refluxed again for an additional 6 hours. The methanol was removed in vacuo and the residue was treated with 80 mL of 1N hydrochloric acid. The mixture was extracted with 4×30 mL of ether, and the pooled extracts were dried over magnesium sulfate and concentrated in vacuo to a green foam. Flash chromatography (40 mm diameter column, 5.5" of 2% phosphoric acid in methanol treated silica gel) afforded 1.15 g (3.36 mmol, 100%) of a pale yellow solid. Recrystallization from 15% ethyl acetate in petroleum ether resulted in 281 mg of white powder. The mother liquor was concentrated and the resulting compound was crystallized from 10% ethyl acetate in petroleum ether. This gave 453 mg of a tan powdery solid which was combined with the first crop affording the title compound which was dried in vacuo at 85° C. for 8 hours: mp 157.5°–159° C.

$^1$H NMR (CDCl$_3$, 400 MHz): δ0.9 (m), 1.7–2.1. (m), 2.5 (m), 2.8 (m), 3.2 (m), 3.83 (s), 3.88 (s), 6.9–7.1 (m), 7.4 (m), 9.0 (m), 9.1 (m).

IR (KBr, cm$^{-1}$): 3350, 3050, 2930, 1700.

Anal. Calcd. for C$_{20}$H$_{26}$N$_2$O$_3$: C, 70.15; H, 7.65; N, 8.18. Found: C, 69.98; H, 7.65; N, 8.10.

Note: The compound appears to be a 3.9:1 mixture of Z:E isomers by NMR.

EXAMPLE 3 cis-1-Ethyl-2,3,4,9-tetrahydro-8-methyl-4-(2-oxopropyl)-1H-carbazole-1-acetic Acid cis-4-(Cyanomethyl)-1-ethyl-2,3,4,9-tetrahydro-8-methyl-1H-carbazole-1-acetic acid (11.9 mmol, 3.67 g, prepared by the process of Example 4) was stirred under nitrogen in 59 mL of anhydrous toluene and treated with 1.19 mmol (305 mg) of Ni(acac)$_2$ (Ni(acac)$_2$.2H$_2$O was dried in vacuo at 100° C. for 16 hours over phosphorous pentoxide). The solution was cooled to 0° C. at which point trimethylaluminum (23.7 mmol, 11.85 mL of a 2N solution in toluene) was added dropwise. The greenish-brown reaction mixture was stirred at room temperature for 24 hours then cooled to 0° C. and treated with another 12 mL of toluene, 305 mg (1.19 mmol) of Ni(aca)$_2$, and 29.63 mmol (14.82 mL of 2N in toluene) of trimethylaluminum. The dark brown reaction mixture was then stirred at room temperature for 72 hours, diluted with 120 mL of ether and quenched slowly with 150 mL of 1N hydrochloric acid. Extraction with ether (4×50 mL), drying (magnesium sulfate) and flash chromatography (50 mm diameter column, 2% phosphoric acid in methanol treated silica gel, 4% ether in methylene chloride eluent) afforded 2.92 g (8.93 mmol, 75%) of a yellow solid. Of this, 1.45 g were recrystallized from 15% ethyl acetate in petroleum ether giving 1.0 g of the title compound as a white powder which was dried in vacuo at 87° over silica for 26 hours; mp 168.5°–169.5° C.

$^1$H NMR (DMSO-d$_6$/400 MHz): δ0.74 (t, 3H, J=7.4 Hz), 1.48–1.56 (m, 1H), 1.64–2.1 (m, 5H), 2.1 (s, 3H), 2.4 (s, 3H), 2.5 (m, 1H), 2.67 (d, 1H, J=14.5 Hz), 2.72 (d, 1H, J=14.5 Hz), 2.91 (dd, 1H, J=3.6, 16.3 Hz), 3.3 (m, 1H), 6.8 (m, 2H), 7.19 (d, 1H, J=7.2 Hz), 10.28 (s, 1H), 11.08 (s, 1H).

IR (KBr, cm$^{-1}$): 3340, 3050, 2960–2880, 1710, 1700.

Anal. Calcd. for C$_{20}$H$_{25}$NO$_3$: C, 73.37; H, 7.69; N, 4.28. Found: C, 73.00; H, 7.81; N, 4.34.

EXAMPLE 4 cis-4-(Cyanomethyl)-1-ethyl-2,3,4,9-tetrahydro-8-methyl-1H-carbazole-1-acetic Acid A solution of cis-1-ethyl-2,3,4,9-tetrahydro-4-[2-(hydroxyimino)ethyl]-8-methyl-1H-carbazole-1-acetic acid methyl ester (7.6 mmol, 2.6 g, prepared by the process of Example 1) in 38 mL of 95% ethanol was stirred at room temperature under nitrogen and treated with six drops of concentrated hydrochloric acid. The solution was then refluxed for 3.5 hours, treated with three drops of concentrated hydrochloric acid, refluxed another hour and treated with another six drops of concentrated hydrochloric acid. After an additional 1.5 hours of reflux, the reaction mixture was concentrated in vacuo and redissolved in 60 mL of ether. The solution was washed with 40 mL of 1N sodium hydroxide and the washing was back-extracted with 2×30 mL of ether. The pooled organic phases were dried over magnesium sulfate and concentrated in vacuo. Flash chromatography (50 mm diameter column, 20% ethyl acetate in petroleum ether eluent) afforded 2.11 g (6.51 mmol, 86%) of the nitrile ester as a pale yellow solid. Of this, 6.42 mmol (2.08 g) were refluxed under nitrogen for 40 minutes in 20.5 mL of ethanol containing 5.1 mL of 2.5N sodium hydroxide (aq). The ethanol was then removed in vacuo and the residue was treated with 120 mL of 1N hydrochloric acid and extracted with 4×50 mL of ether. Drying (magnesium sulfate) and concentration in vacuo afforded 1.97 g (6.35 mmol, 99% crude yield) of a greenish-grey solid. Recrystallization from methanol-water gave 1.4 g of the title compound as a tan solid which were dried in vacuo over phosphorous pentoxide at 87° C. for 24 hours: mp 205.5°–207° C.

$^1$H NMR (DMSO-d$_6$, 400 MHz): δ0.71 (t, 3H, J=7.4 Hz), 1.7–2.34 (m, 6H), 2.43 (s, 3H), 2.66–2.82 (m, 3H), 2.9–2.96 (m, 1H), 3.24 (m, 1H), 6.8–6.86 (m, 2H), 7.35 (d, 1H, J=7.1 Hz), 10.4 (s, 1H), 11.0 (s, 1H).

IR (KBr, cm$^{-1}$): 3375, 3060, 3020, 2970, 2930, 2250, 1700.

Anal. Calcd. for $C_{19}H_{22}N_2O_2$: C, 73.52; H, 7.14; N, 9.02. Found: C, 73.83; H, 7.36; N, 8.95.

We claim:

1. The method for the production of a compound of formula (I)

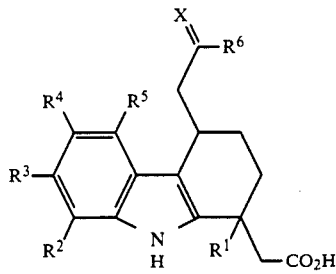

wherein $R^1$ is lower alkyl containing one to six carbon atoms; $R^2$ to $R^5$ are independently selected from the group consisting of H, lower alkyl containing one to six carbon atoms, halogen and haloalkyl containing one to six carbon atoms; $R^6$ is H; X is NOH or NO-alkyl wherein alkyl contains one to six carbon atoms consisting essentially of a) treating a compound of formula (VII)

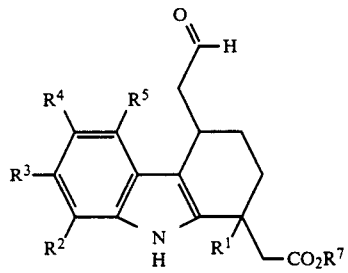

wherein $R^1$ to $R^5$ are as defined above; and $R^7$ is lower alkyl containing one to six carbon atoms, with hydroxylamine hydrochloride to form the ester of a compound of formula (I) wherein $R^1$ to $R^5$ are as defined above; $R^6$ is H and X is NOH or treating said compound of formula (VII) with alkyl-ONH$_2$.HCl to form the ester of a compound of formula (I) wherein $R^1$ to $R^5$ are as defined above; $R^6$ is H and X is NO-alkyl and b) hydrolyzing said ester to obtain a compound of formula (I) wherein $R^1$ to $R^6$ are defined above.

2. The method for the production of a compound of formula

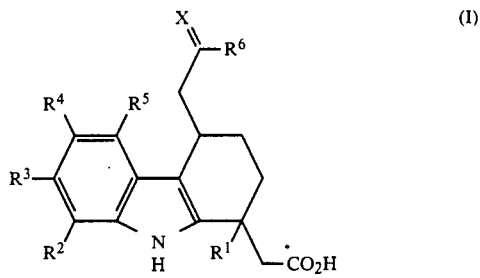

wherein $R^1$ is lower alkyl containing one to six carbon atoms; $R^2$ to $R^5$ are independently selected from the group consisting of H, lower alkyl containing one to six carbon atoms, halogen and haloalkyl containing one to six carbon atoms; $R^6$ is lower alkyl containing one to six carbon atoms; and X is NOH or NO-alkyl containing one to six carbon atoms consisting essentially of reacting the ketone compound of formula

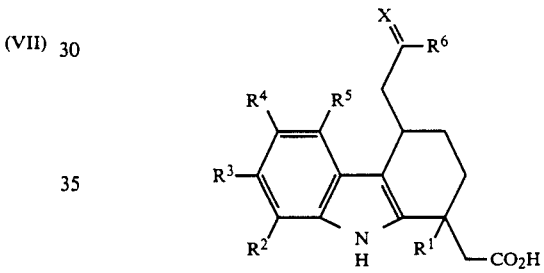

wherein $R^1$ to $R^6$ are as defined above and X is O with hydroxylamine hydrochloride to form the compound of formula (I) wherein $R^1$ to $R^6$ are as defined above and X is NOH or reacting said ketone compound with alkyl-ONH$_2$.HCl to form the compound of formula (I) wherein $R^1$ to $R^6$ are as defined above and X is NO-alkyl.

* * * * *